(12) United States Patent
Lamoncha

(10) Patent No.: US 11,107,026 B2
(45) Date of Patent: *Aug. 31, 2021

(54) SYSTEM AND METHOD FOR INCREASING EMPLOYEE PRODUCTIVITY THROUGH CHALLENGES

(71) Applicant: Mark Lamoncha, Columbiana, OH (US)

(72) Inventor: Mark Lamoncha, Columbiana, OH (US)

( * ) Notice: Subject to any disclaimer, the term of this patent is extended or adjusted under 35 U.S.C. 154(b) by 51 days.

This patent is subject to a terminal disclaimer.

(21) Appl. No.: 16/453,345

(22) Filed: Jun. 26, 2019

(65) Prior Publication Data

US 2019/0318289 A1 Oct. 17, 2019

Related U.S. Application Data

(63) Continuation-in-part of application No. 15/591,795, filed on May 10, 2017, now Pat. No. 10,885,487, which is a continuation of application No. 12/748,895, filed on Mar. 29, 2010, now Pat. No. 9,659,269.

(Continued)

(51) Int. Cl.
*G06Q 10/06* (2012.01)
*A63F 13/50* (2014.01)

(52) U.S. Cl.
CPC ....... *G06Q 10/06398* (2013.01); *A63F 13/50* (2014.09); *G06Q 10/0639* (2013.01); *G06Q 10/06393* (2013.01); *G06Q 10/063114* (2013.01)

(58) Field of Classification Search
CPC ........ G06Q 10/06398; G06Q 10/0639; G06Q 10/06393; G06Q 10/063114
See application file for complete search history.

(56) References Cited

U.S. PATENT DOCUMENTS 3,035,355 A 5/1962 Holmes
3,967,261 A 6/1976 Fudaley
(Continued)

FOREIGN PATENT DOCUMENTS

DE 202005014694 U1 6/2006

OTHER PUBLICATIONS

Lazear, E., Performance Pay and Productivity, The American Economic Review, Dec. 2000, pp. 1346-1361, vol. 90, No. 5.
(Continued)

*Primary Examiner* — Matthew S Gart
*Assistant Examiner* — Stephen S Swartz
(74) *Attorney, Agent, or Firm* — Standley Law Group LLP

(57) ABSTRACT

Systems and methods are provided for increasing employee productivity in a production process. One or more machines for accomplishing a production activity and in communication with a database which includes pay rates and predetermined thresholds for the production activity. Data acquiring devices associated with each machine measure production rates in substantially real time. A processor retrieves the pay rate and the production rate to determine a real-time-pay rate. A display provides a ranking and visualization reflecting each employee's real-time-pay and a graphic indicating whether each employee's real-time-pay rate exceeds one or more of the predetermined thresholds.

19 Claims, 10 Drawing Sheets

Related U.S. Application Data

(60) Provisional application No. 61/164,220, filed on Mar. 27, 2009.

(56) References Cited

U.S. PATENT DOCUMENTS

| | | | |
|---|---|---|---|
| 4,179,611 | A | 12/1979 | Mill et al. |
| 4,408,204 | A | 10/1983 | Salvesen |
| 4,615,197 | A | 10/1986 | Allebach |
| 4,800,502 | A | 1/1989 | Steward et al. |
| 5,134,574 | A | 7/1992 | Beaverstock |
| 5,429,373 | A | 7/1995 | Chelko et al. |
| 5,459,657 | A | 10/1995 | Wynn et al. |
| 5,461,570 | A * | 10/1995 | Wang ............ A61L 2/24 700/110 |
| 5,717,867 | A | 2/1998 | Wynn et al. |
| 5,754,965 | A | 5/1998 | Hagenbuch |
| 5,842,182 | A | 11/1998 | Bonner et al. |
| 6,034,970 | A | 3/2000 | Levac et al. |
| 6,119,097 | A | 9/2000 | Ibarra |
| 6,125,356 | A | 9/2000 | Brockman et al. |
| 6,160,528 | A | 12/2000 | Carpine et al. |
| 6,336,053 | B1 | 1/2002 | Beatty |
| 6,347,306 | B1 | 2/2002 | Swart |
| 6,356,875 | B1 | 3/2002 | Green et al. |
| 6,507,765 | B1 | 1/2003 | Hopkins et al. |
| 6,681,197 | B2 | 1/2004 | Brunner |
| 6,815,650 | B1 | 11/2004 | Barzt |
| 7,114,648 | B2 | 10/2006 | Ginskey et al. |
| 7,197,638 | B1 | 3/2007 | Grawrock et al. |
| 7,228,192 | B2 | 6/2007 | Popplewell |
| 7,249,051 | B1 | 7/2007 | Jenniges et al. |
| 8,015,454 | B1 | 9/2011 | Harrison et al. |
| 8,040,292 | B2 | 10/2011 | Ronzani et al. |
| 8,209,243 | B2 | 6/2012 | Smith et al. |
| 9,659,269 | B2 | 5/2017 | Lamoncha |
| 2002/0038235 | A1 * | 3/2002 | Musafia ............ G06Q 10/10 705/7.25 |
| 2002/0091498 | A1 | 7/2002 | Brunner et al. |
| 2002/0103569 | A1 | 8/2002 | Mazur |
| 2002/0143423 | A1 | 10/2002 | Huber et al. |
| 2002/0165749 | A1 | 11/2002 | Northcutt et al. |
| 2003/0014498 | A1 | 1/2003 | Kreidler et al. |
| 2003/0167238 | A1 * | 9/2003 | Zeif ............ G06Q 99/00 705/400 |
| 2003/0233163 | A1 | 12/2003 | Dorsch |
| 2004/0044733 | A1 | 3/2004 | Fan |
| 2004/0148136 | A1 | 7/2004 | Sasaki et al. |
| 2004/0210475 | A1 * | 10/2004 | Starnes ............ G06Q 10/105 705/320 |
| 2005/0130633 | A1 | 6/2005 | Hill et al. |
| 2005/0137735 | A1 | 6/2005 | Loy et al. |
| 2005/0149216 | A1 * | 7/2005 | Popplewell ............ G05B 19/12 700/96 |
| 2005/0165585 | A1 | 7/2005 | Bhateja et al. |
| 2006/0010051 | A1 | 1/2006 | Sattler et al. |
| 2006/0020509 | A1 | 1/2006 | Strain et al. |
| 2006/0259160 | A1 | 11/2006 | Hood et al. |
| 2007/0050238 | A1 * | 3/2007 | Carr ............ G06Q 10/10 |
| 2007/0205861 | A1 | 9/2007 | Nair et al. |
| 2009/0192926 | A1 | 7/2009 | Tarpata |
| 2009/0204234 | A1 | 8/2009 | Sustaeta et al. |
| 2010/0153263 | A1 | 6/2010 | Keadle et al. |

OTHER PUBLICATIONS

Ludwig, T. D. et al., Enhancing Incentive Programs with Proximal Goals and Immediate Feedback: Engineered Labor Standards and Technology Enhancements in Stocker Replenishment, Journal of Organizational Behavior Management, 2007, pp. 33-68, 27 (1).

* cited by examiner

SYSTEM AND METHOD FOR INCREASING EMPLOYEE PRODUCTIVITY THROUGH CHALLENGES

CROSS REFERENCE TO RELATED APPLICATIONS

This application is a continuation-in-part of U.S. application Ser. No. 15/591,795 filed May 10, 2017, which is a continuation of U.S. application Ser. No. 12/748,895, filed Mar. 29, 2010, which issued as U.S. Pat. No. 9,659,269 on May 23, 2017, which claims priority to U.S. Provisional Application No. 61/164,220 filed Mar. 27, 2009, the disclosures of each of which are hereby incorporated by reference as if fully recited herein.

TECHNICAL FIELD

Exemplary embodiments of the present invention are generally directed to a system and method for increasing employee productivity. More particularly, exemplary embodiments of the present invention are generally directed to a system and method for increasing employee productivity by illustrating the employee's pay rate directly to the employee, preferably in a fashion which indicates the employee's progress relative to peers or co-workers.

BACKGROUND AND SUMMARY OF THE INVENTIVE FIELD

In any workplace setting the productivity of each individual is vital to the overall success of the company. In any workplace setting, the main way to increase the profitability of the company is to measure and increase the productivity of each and every employee. There have been numerous studies and countless amounts of research performed to find ways to increase employee productivity. The results of such studies and research indicate that a one important way to increase employee productivity is to provide each and every employee with incentive to safely increase both the quantity and quality of their work output. This may be accomplished by giving each employee personal responsibility within the process for the amount and quality of work they perform.

Oftentimes, in the workplace setting, the personal responsibility of employees consists primarily of meeting certain standards, expectations or goals during their scheduled work time. Furthermore, employees typically get paid by an hourly or salary rate. Consequently, employees have no real incentive to perform at any levels higher than the minimum goal number; as they will be paid the same amount of money regardless of any excess amount of output over the minimum goal. Accordingly, these employees see a disconnect between their individual increase in output and their improvements in safety, quality and productivity.

Normally, employers provide incentives to employees by providing compensation through increases in hourly rates, salary, or periodic bonuses. However, many employees do not consider these as adequate forms of compensation. It may take weeks, months or even years of increased productivity before an employee is recognized for the fruits of his or her individual labor, if they are even so recognized. Furthermore, on a weekly or even shift basis, most employees do not have a way to evaluate if or how they may be adequately compensated if they go above the call of duty and perform above the minimum goals. Furthermore, many employees trust management to adequately compensate them for their increased productivity. This sometimes results in employees who perform just well enough not to get fired, as they are left feeling that any increased productivity will not be adequately rewarded.

Consequently, it can be understood that there is a need for a system and method for increasing employee productivity. Preferably, such a system and method would provide employees with real-time incentives to safely increase the amount and quality of their individual output. It would also be preferable that such a system and method would make each employee individually accountable for the amount of compensation they earn. Preferably, such a system and method may also provide timely monetary compensation for employees. Additionally, it is preferred that the system and method may have integrated safety and quality systems. A system and method of an exemplary embodiment of the system and method for increasing employee output may satisfy all or some of these needs/preferences.

In combination with, or separate from giving each employee personal responsibility within the process for the amount and quality of work they perform, productivity can be improved by making an activity fun and engaging. One way of making a task fun and engaging is to draw upon the individual's competitive spirit. Therefore, there is a need for a system and method which increases employee productivity through challenges.

A system and method are provided for igniting the spirit of human competition within the worker by encouraging them to safely increase productivity translating to their increased monetary compensation and their reward of meeting and beating production goals without sacrificing quality. More particularly, in one exemplary system and method employee competition is increased by illustrating the employee's pay rate in "real time" directly to a system that displays on any electronic device, stationary or portable, such as on a pay rate watch.

Generally speaking, an exemplary embodiment of the computerized system and method for increasing employee productivity provides a database for storing data, a data input device for inputting expected output parameters or other metrics into the database and a data acquiring device for acquiring actual output data or other metrics during performance of any workplace duties, preferably in real-time. The data acquiring device may be linked by an interface that transfers the acquired data to the database, where a processor may evaluate the inputted data versus the acquired data. The processor is connected to a data displaying device that may display the inputted, acquired and evaluated data, preferably in real-time.

Preferably, the system and method include a data correcting device for correcting the actual production data after the production data has been acquired. It may be preferred that an exemplary embodiment includes a network that links to a machine's PC to the machine's PLC. In some exemplary embodiments, the machine's PLC may be controlled by and interrupted by the machine's PC for safety and quality related training and/or warnings in the form of e-mails and training presentation software. In some embodiments, the machine's PC allows a user to correct actual production data and shut down the machine. It is also preferred that an embodiment may include any portable or stationary data displaying device or any pay rate watch device adapted to secure around a user's wrist and is adapted to link with the processor. In another embodiment, the system and method include a safety and quality control system that is adapted to lockout the machine whenever the employee identification number is not on an approved list of employee identification numbers stored in the database. In another embodiment, the system and method may link with a banking system for distributing a daily payroll or direct deposit of an employee's earned wages.

In other exemplary embodiments, the employee's competitive spirit is, alternatively or additionally, engaged through challenges. In exemplary systems and methods disclosed herein, the employee's increase or decrease in payrate, productivity, or other metrics may be translated into actions on an electronic display as part of a challenge which may indicate the employees progress relative to his or her peers or co-workers. The electronic display may be associated with the employee's machine. Additionally, or alternatively, the electronic display may be located in a common area and may be in electronic communication with a number of employee's machines. Each employee may compete with himself or herself. Alternatively, or additionally, each employee may compete against one another. In still other exemplary systems and methods, an animated physical device may be used instead of, or in addition to, the electronic display.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Figure 1:
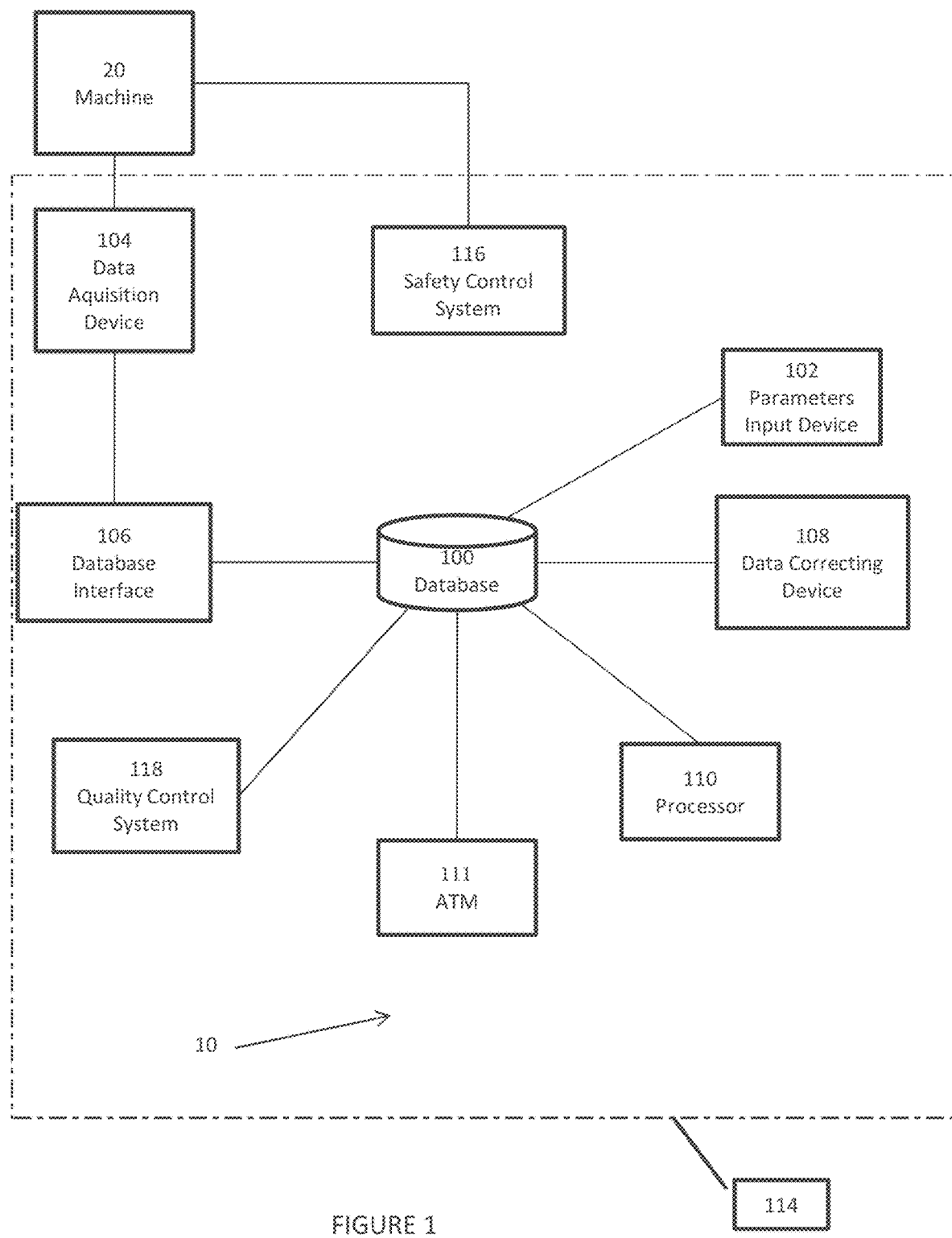
FIG. 1 is a schematic view illustrating one exemplary embodiment of a system for increasing employee productivity in a production process on a machine.
Figure 2:
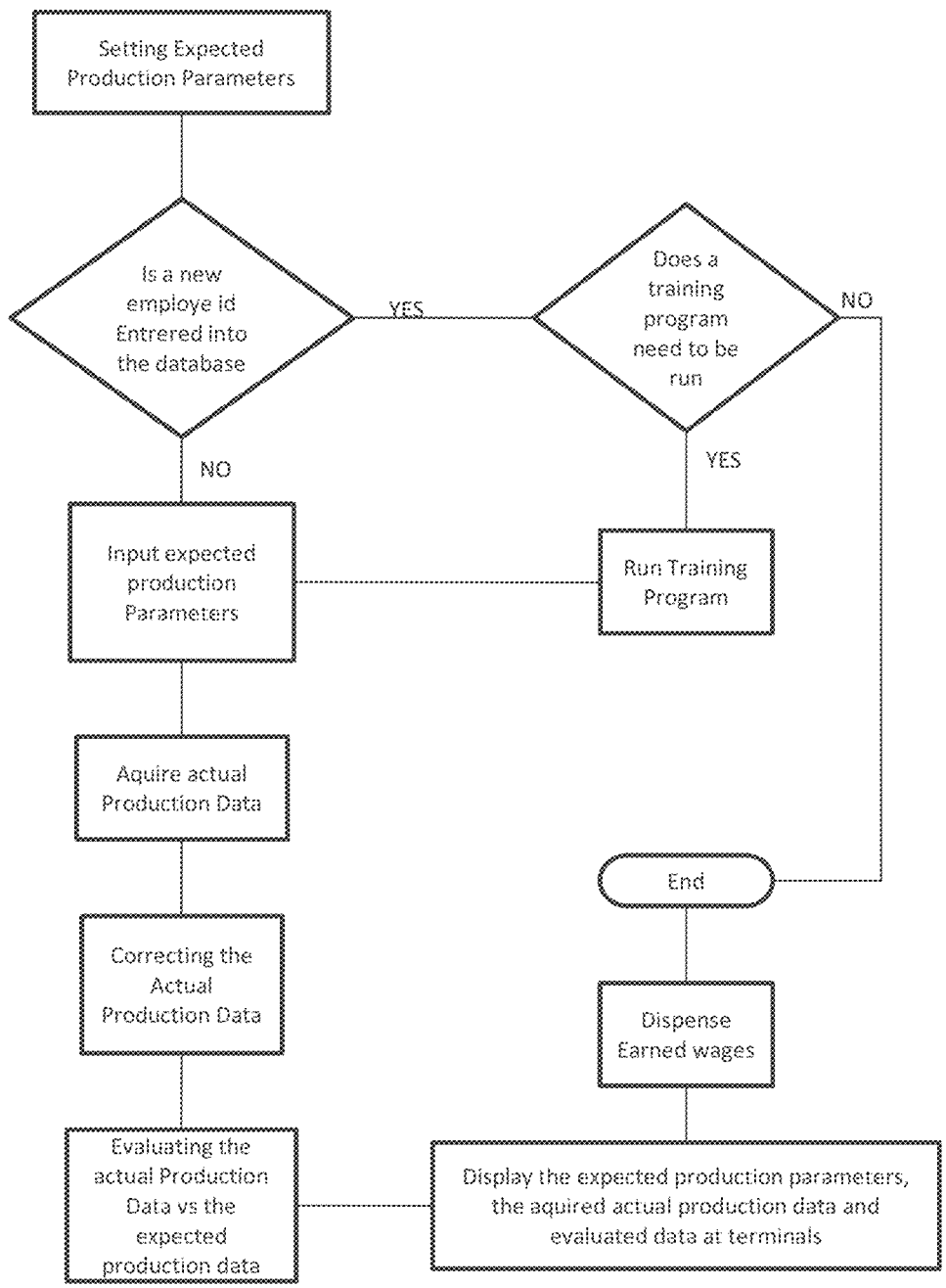
FIG. 2 is a flow diagram illustrating the steps of an exemplary embodiment of the method for increasing employee productivity in a production process on a machine.

FIG. 1 depicts a schematic of one exemplary embodiment of a system 10 for increasing employee productivity in a production process on a machine 20. The machine 20 may be any type of machine for accomplishing any kind of production activity. Similarly, FIG. 2 is flow diagram illustrating the steps of an exemplary embodiment of the method for increasing employee productivity in a production process on the machine 20. As shown, this particular system 10 comprises a database 100 for storing data, a data inputting device 102 for inputting expected production parameters into the database 100, a data acquiring device 104 for acquiring actual production data from the machine 20, an interface 106 for transferring the acquired production data to the database 100, and a data correcting device for correcting actual production data 108 after the production data is acquired. Additionally, the illustrated embodiment of the system 10 includes a processor 110 for evaluating the inputted data versus the acquired data, a data displaying device 112 for displaying the inputted, acquired and evaluated data, a computer network 114 that links the machine to the database 100, and the data displaying device 112, a safety control system 116, a quality control system 118, and an automated telling machine 120, though such components are not necessarily required in all embodiments.

In the illustrated embodiment, a data inputting device 102 for inputting expected production parameters or other metrics into the database 100 for storing data is a computer terminal that is in connection with the database 100. Typically, production parameters that may be inputted in the database 100 include, but are not limited to: standard time to fabricate an individual part; standard rate of pay per part; standard pay rate per minute, hour, shift, week, month, year; standard number of parts fabricated in a minute, hour, shift, week, month, year; employee's name; employee's identification from fingerprints, retinal scan, DNA, etc.

The system 10 includes a data acquiring device 104 for acquiring actual production data or other metrics from the machine 20, which in this particular embodiment, is a programmable logic controller that is linked to multiple sensors. Typically, actual production data acquired may include, but is not limited to: total parts produced per second, minute, hour, shift, week, month, year; scrap rate per second, minute, hour, shift, week, month, year; total machine run time; runtime per part, shift, week, month, year; total machine downtime; downtime per part, shift, week, month, year; product quality data; machine safety data, etc. Typically, but not necessarily, the actual production data may be acquired automatically and in substantially real-time.

Furthermore, in this particular embodiment, an interface 106 transfers the acquired production data to the database 100. The interface 106 may be any type of connection that includes, but is not limited to: cable or telephone lines, the Internet, satellite links, etc. In this particular embodiment, the interface 106 is wired. However, in other exemplary embodiments, the interface 106 may be wireless.

Although it is preferred that an embodiment of the system 10 includes a data correcting device 108 for correcting actual production data after the production data is acquired, it is not required. In this embodiment, the data correcting device 108 is a computer terminal that is in connection with the database 100. Preferably, but not necessarily, the computer terminal is the same computer terminal used to input production parameters. In other embodiments, the data correcting device 108 may be a keypad or keyboard linked with a programmable logic controller.

This particular embodiment includes a processor 110 for evaluating the inputted production parameters versus the acquired production data to produce evaluated data. The processor 110 may execute algorithms to produce the evaluated data. The following are some examples of algorithms that may be performed by the processor 110 given the inputted production parameters and the acquired data. These examples are in no way limiting the capability of the numerous different algorithms the processor 110 may execute. One simple example of a typical algorithm executed by the processor may produce the total realized pay for an employee for a shift that could be set forth in a relationship such as, but not limited to:

$$TRPS = X * TPPS$$

where:
TRPS is the total realized pay for an employee for a shift;
X is the standard pay rate per part; and
TPPS is the total parts produced for a shift.

In this example, the standard pay rate per part would be inputted into the database 100 as one of the performance parameters and the total parts produced for a shift would be actual data acquired from the machine during the production process.

In another example, the algorithm may produce the difference between expected pay per shift and the realized pay per shift that could be set forth in a relationship such as, but not limited to:

$$DEPRP = X * TPPS - EPS$$

where:
DEPRP is the difference between the expected pay and realized pay per shift
X is the standard pay rate per part;
TPPS is the total parts produced for a shift; and
EPS is the expected pay per shift.

In this example, the standard pay rate per part and the expected pay per shift would be inputted into the database 100 as one of the performance parameters and the total parts produced for a shift would be actual data acquired from the machine during the production process.

In another example, the algorithm may produce the realized hourly rate by an employee that could be set forth in a relationship such as, but not limited to:

$$RHR = [TPPS/T] * X$$

where:
RHR is the realized hourly rate
TPPS is the total parts produced for a shift;
T is total time in hours; and
X is the standard pay rate per part.

In this example, the standard pay rate per part would be inputted into the database 100 as one of the performance parameters and the total parts produced for a shift and the total time in hours would be actual data acquired from the machine during the production process.

Normally, the processor 110 may produce evaluated data including, but is not limited to: difference between expected pay and realized pay per second, minute, hour, shift, week, month, year; realized pay per minute, hour, shift, week, month year; realized pay-rate per hour, shift, week, month, year; difference between expected and realized parts produced per minute, hour, shift, week, month, year; quality data, and safety data. Typically, but necessarily, the evaluated data is produced automatically and in real-time.

Figure 3:
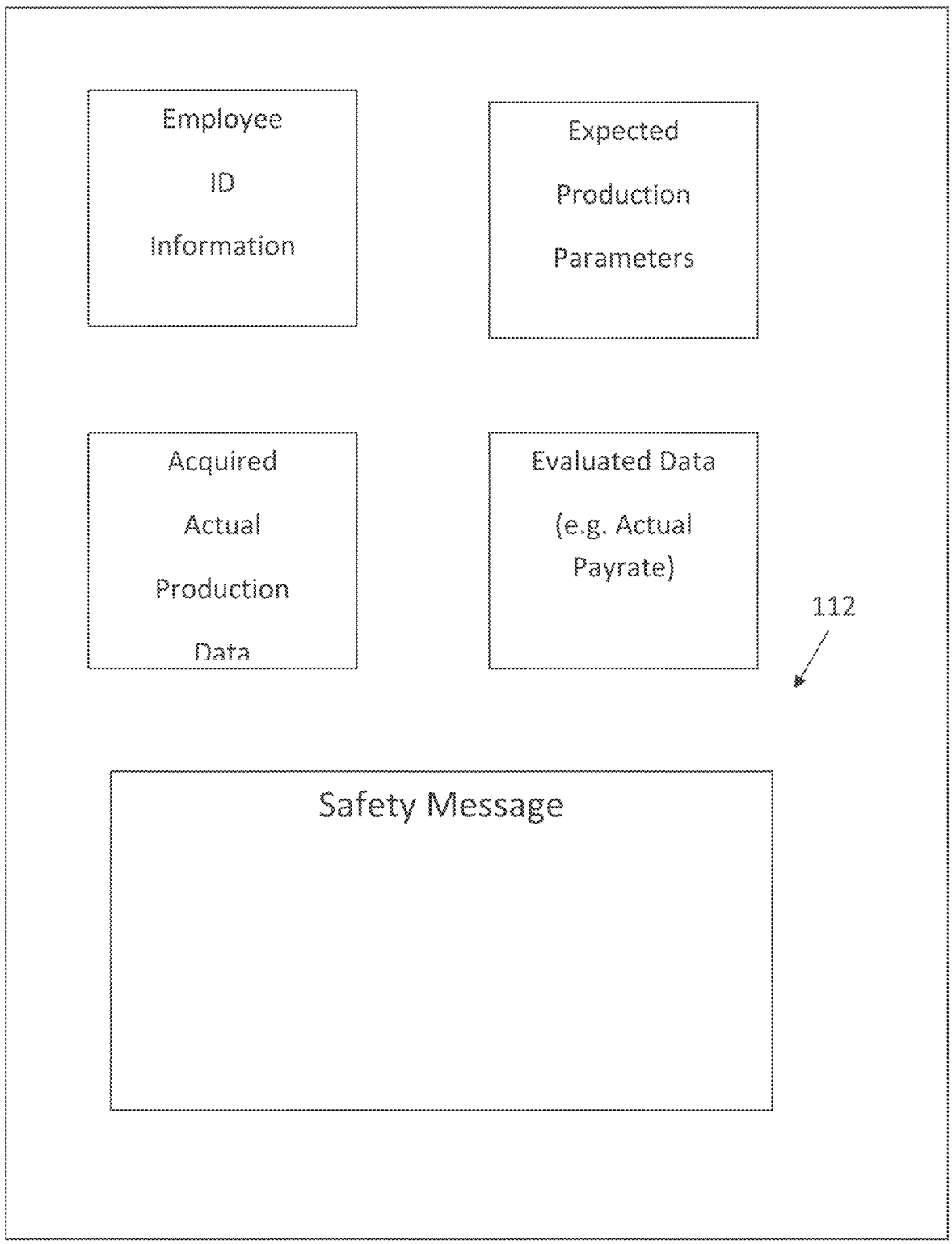
FIG. 3 is a screenshot illustrating an exemplary embodiment of the means for displaying data.

In one particular embodiment, the system 10 includes a data displaying device 112 that may display the inputted, acquired and evaluated data that is adapted to connect to the database 100. An example of a screenshot of an exemplary embodiment of the data displaying device is illustrated in FIG. 3. In this particular embodiment, the means for displaying 112 is an electronic display. Preferably, but not necessarily, the data displaying device 112 is located within visible sight of the employee operating the machine 20 to help provide incentive to the employee to increase both production rate and quality. In this regard, the data displaying device 112 may be a portable device that is adapted to connect to the database 100 using a wireless network. Preferably, but not necessarily, the portable display device may be adapted to secure around an individual's wrist, the result being a device that may resemble a wristwatch. In another embodiment, the portable device may be adapted to secure to an individual's belt. However, in other embodiments, the data displaying device 112 may be any type of display screen that may be adapted to connect to the database 100 through a wireless or wired connection. In one exemplary embodiment, the data displaying device 112 may be a monitor for a computer. In some exemplary embodiments, the data displaying device 112 is engaged with and adjacent to the machine 20 on an assembly line or in the employee's workstation to ignite the spirit of human competition within the worker by encouraging them to safely increase productivity translating to their increased monetary compensation and their reward of meeting and beating production goals without sacrificing quality.

In whatever form, all the components of the system 10 are preferably linked by a network 114. However, the network 114 may link any and/or all components of the system 10. One skilled in the art would realize that there are many different ways to network the components, including, but not limited to: cable or telephone lines, the Internet, satellite links. In this particular embodiment, the network is wireless. However, in other exemplary embodiments, the network 114 may be wired and/or wireless, depending upon the design factors and other considerations, as would be understood by one skilled in the art.

In this particular embodiment, the system 10 includes a safety control system 116 adapted to communicate with the machine. Although the safety control system 116 is preferred, other exemplary embodiments of the system 10 may not include such a safety control system 116. In one particular embodiment, the safety control system 116 may have a terminal wherein an individual may input an individual identification code. In this embodiment, depending upon the identification code entered, the machine may lockout whenever the employee identification number is not on a secured list in the database.

In other exemplary embodiments, the safety and quality control system 116 may control a machine's PLC and interrupt operation of the machine. In this particular embodiment, the safety control system 116 is controlled by a PC. In some embodiments, the safety control system 116 may interrupt the machine's PC for safety or quality related training and/or warnings in the form of emails and training presentation software. In one example, at the start of a shift, the safety control system 116 may walk a worker through a training exercise before the worker may start working. In another example, an administrator or another authorized individual may send the machine's PC an email message that must be read by a worker before the machine will start or continue operating.

In order to provide timely incentive rewards for employees, a banking system 111 for distributing a daily payroll or direct deposit of an employee's earned wages may be linked with the system 10 to provide an amount of money earned by the employee. In this particular embodiment, an individual may obtain the amount of money they earned from an automated telling machine at the end of each production shift. However, in other embodiments, the banking system 111 may allow the employee to obtain the amount of money they earned at varying time intervals, such as, but not limited to: each hour, daily, weekly, monthly, yearly or each break period. In yet another embodiment, the banking system 111 may provide other forms of compensation by itself, or in addition to monetary compensation. One example may be where the banking system 111 may provide employees with tokens that the employee may spend at a company store. In other embodiments, the banking system 111 may directly deposit the employee's earned wages into a predetermined banking or checking account.

Figure 4:
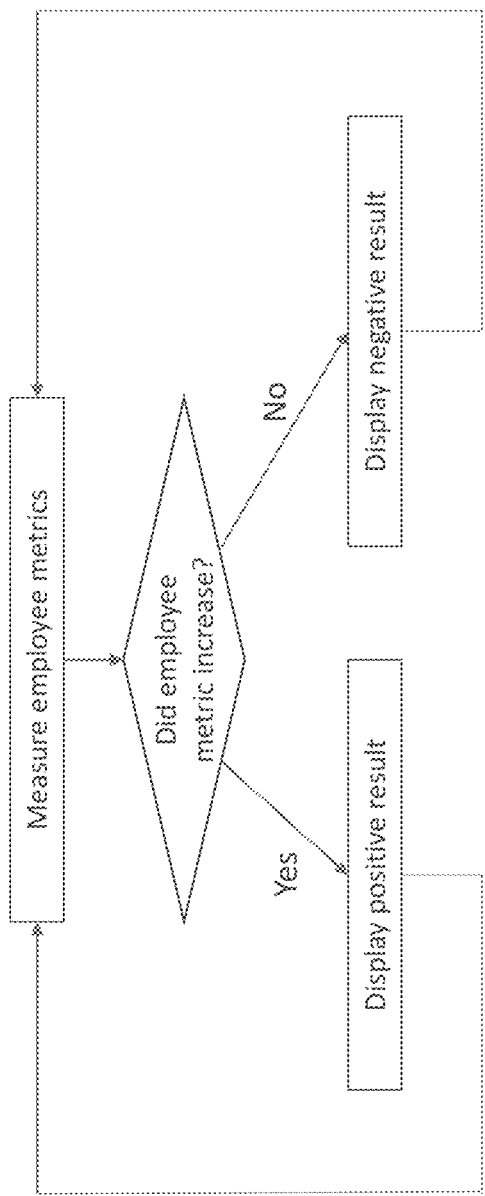
FIG. 4 is a flow diagram illustrating exemplary logic for challenges.

FIG. 4 is a flow diagram illustrating exemplary logic for the challenge system 10. Various employee metrics may be measured. For example, without limitation, such metrics may be measured by way of the data acquisition device 104 and may comprise actual production data. Such actual production data may include, but is not limited do: total parts produced per second, minute, hour, shift, week, month, year; scrap rate per second, minute, hour shift, week, month, year; total machine run time; runtime per part, shift, week, month, year; total machine downtime; downtime per part, shift, week, month, year; product quality data; machine safety data, etc. Additionally, or alternatively, such metrics may be measured by way of the processor 110 and may comprise real-time-pay rate. Such metrics may be measured periodically, continuously, at regular or irregular intervals, and/or in substantially real time. The measured employee metrics may be stored at the database 100, though such is not required. In still other exemplary embodiments, the metric may be compared against one or more-predetermined thresholds.

The measured employee metrics may be compared against previously measured metrics. Such comparison may be made at the processor 110, though such is not required. If the measured metric has increased as compared to a previously measured metric, a positive result may be displayed. If the measured metric has decreased, a negative result may be displayed. However, it is notable that it may be desirable to decrease some metrics and undesirable to increase some metrics. In such cases, a positive result may be displayed where a measured metric has decreased and a negative result may be displayed where a measured metric has increased. An example of such a situation is the production of defective units.

Figure 5:
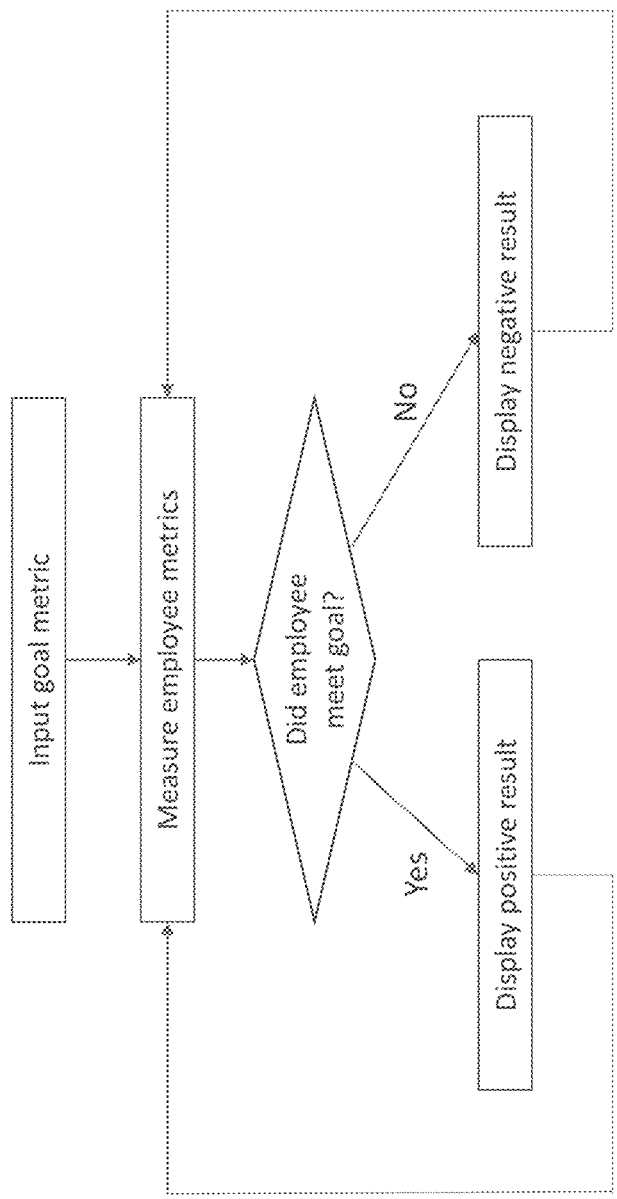
FIG. 5 is a flow diagram illustrating other exemplary logic for challenges.

FIG. 5 illustrates other exemplary logic for the challenge system 10. A goal metric may be inputted. In exemplary embodiments, the goal metric may be inputted by way of the data input device 102 and may be stored at the database 100, though such is not required. The measured employee metrics may be compared against the goal metric. Such comparison may be made at the processor 110, though such is not required. If the measured metric has met or exceeded the goal, a positive result may be displayed. If the measured metric has not met the goal, a negative result may be displayed. However, it is notable that the goal may be a minimum, maximum, rate over time, relative goal, some combination thereof, or the like. It is further notable that the goal may be one of the employee's previously measured metrics. In still other exemplary embodiments, the metric may be compared against one or more-predetermined thresholds.

Figure 6:
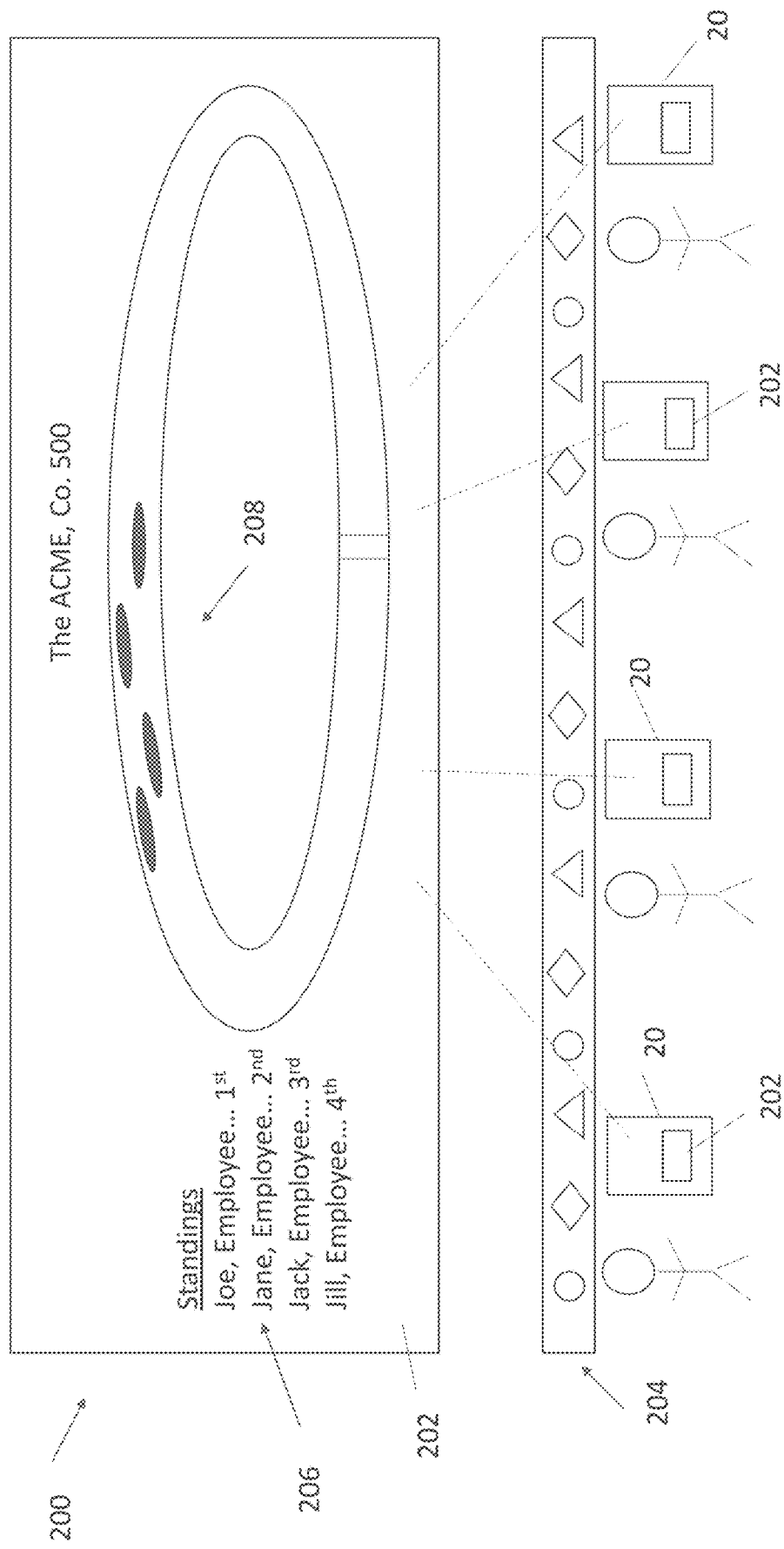
FIG. 6 is an exemplary challenge system for reflecting employee metrics.

FIG. 6 is an exemplary challenge system 200 for reflecting employee metrics and/or progress relative to peers or co-workers. The challenge system 200 may comprise one or more electronic displays 202. In exemplary embodiments, an electronic display 202 may be provided on each machine 20. Alternatively, or additionally, a single electronic display 202 may be placed in electronic communication with a number of machines 20. In the illustrated example, which is merely exemplary and is not intended to be limiting, each machine 20 is associated with a given assembly line 204 and is placed in electronic communication with the challenge system 200 comprising the electronic display 202 such that all employees working on the assembly line 204 may compete against one another. The challenge system 202 may be configured to receive the metrics and determine whether a positive or negative result should be displayed. Alternatively, or additionally, the challenge system 202 may instead receive a notification of whether a positive or negative result should be displayed. For example, without limitation, such determination of a positive or negative result may be made at the processor 110.

The challenge system 200 may be configured to display the positive or negative result for each employee. In exemplary embodiments, such updates may be made in substantially real-time so that the employees receive immediate feedback regarding their work. Such positive and negative results may be reflected in a point system, a ranking, a movement or action, some combination thereof, or the like.

For example, without limitation, the electronic display 202 may be configured to display a simulated race. As positive and negative results are determined, the employee's relative standings 206 may be changed and the same may be reflected on a simulated race track 208. In this way, employees may compete against one another. The electronic display 202 may be placed in a common area such as on the ceiling, on a wall, in a break room, on the factory floor, some combination thereof, or the like. Of course, this is just one example which is not intended to be limiting. For example, without limitation, the simulated race may reflect each employee's real-time-pay rate, though any metric is contemplated.

Figure 7:
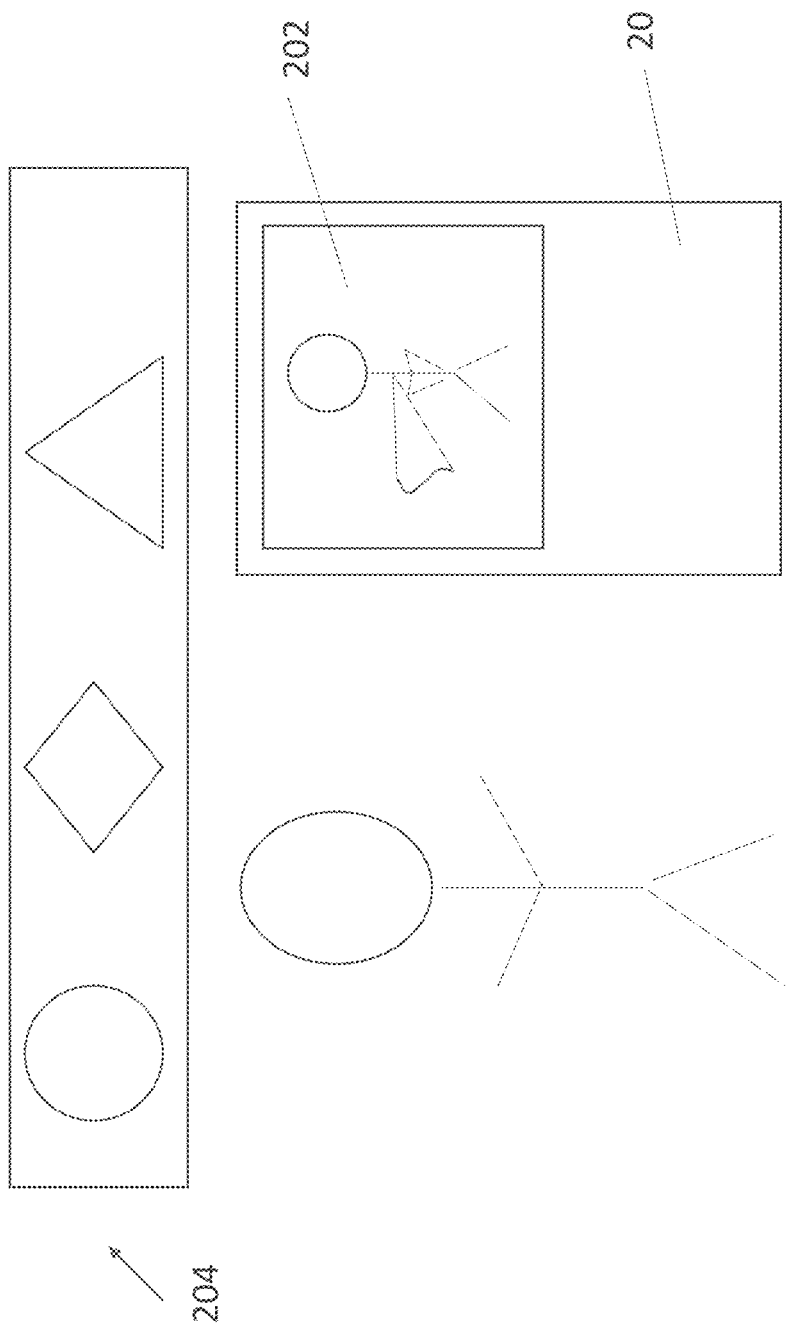
FIG. 7 is another exemplary challenge system for reflecting employee metrics.

FIG. 7 is another exemplary challenge system 200 for reflecting employee metrics. In the illustrated embodiment, the electronic display 202 is provided on, or associated with, an individual machine 20. As positive or negative results are determined, the challenge system 200 may be configured to display positive and negative actions on the electronic display 202. In exemplary embodiments, an action hero may complete various tasks, gain components of a hero's outfit, or the like. Of course, this is just one example and is not intended to be limiting. In this way, the employee may compete against himself or herself or some predetermined criteria. For example, without limitation, the action hero's outfit and/or actions may reflect the employee's real-time-pay rate, though any metric is contemplated.

Figure 8:
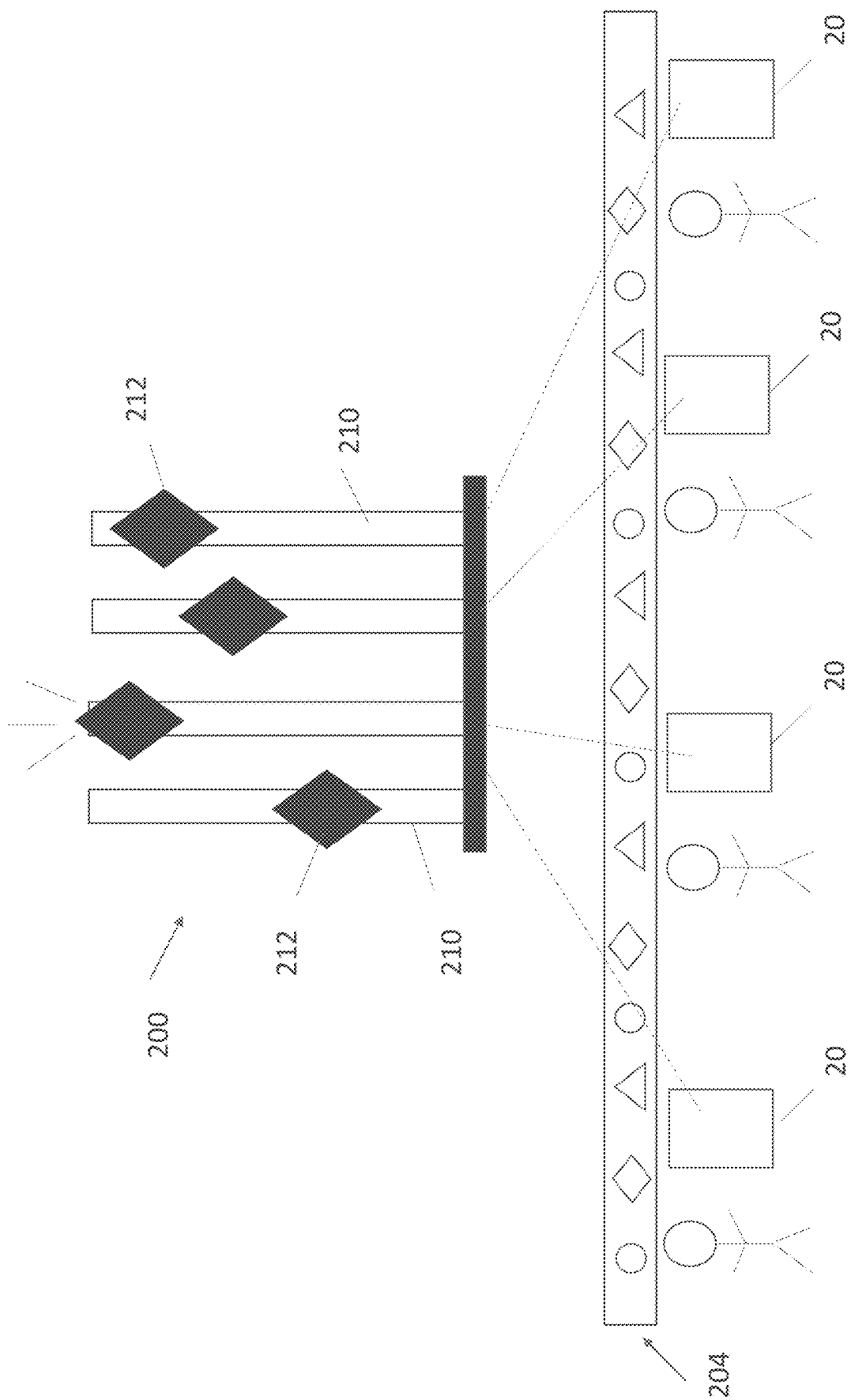
FIG. 8 is another exemplary challenge system for reflecting employee metrics.

FIG. 8 is another exemplary challenge system 200 for reflecting employee metrics. The challenge system 200 may comprise an animated physical system configured to reflect the positive or negative results. In the illustrated embodiment, a number of poles 210 are provided, each having an object 212. As positive or negative results are determined, the challenge system 200 may be configured to move the object 212 up or down the pole to reflect the positive and negative results. In exemplary embodiments, a pole 210 comprising an object 212 may be provided for each machine 20 in communication with the challenge system 200 such that the employees may compete against one another. In other exemplary embodiments, a single pole 210 and object 212 may be provided for a group of machines 20 and/or employees such that employee's collective efforts may be reflected against themselves or against another group of machines 20 and/or employees. Of course, the use of poles 210 and objects 212 are merely exemplary and is not intended to be limiting. For example, in other exemplary embodiments, an animatronic person, event, object, animal, some combination thereof, or the like, may be utilized. For example, without limitation, the movement of the object 212 may reflect the employee's real-time-pay rate, though any metric is contemplated.

Figure 9:
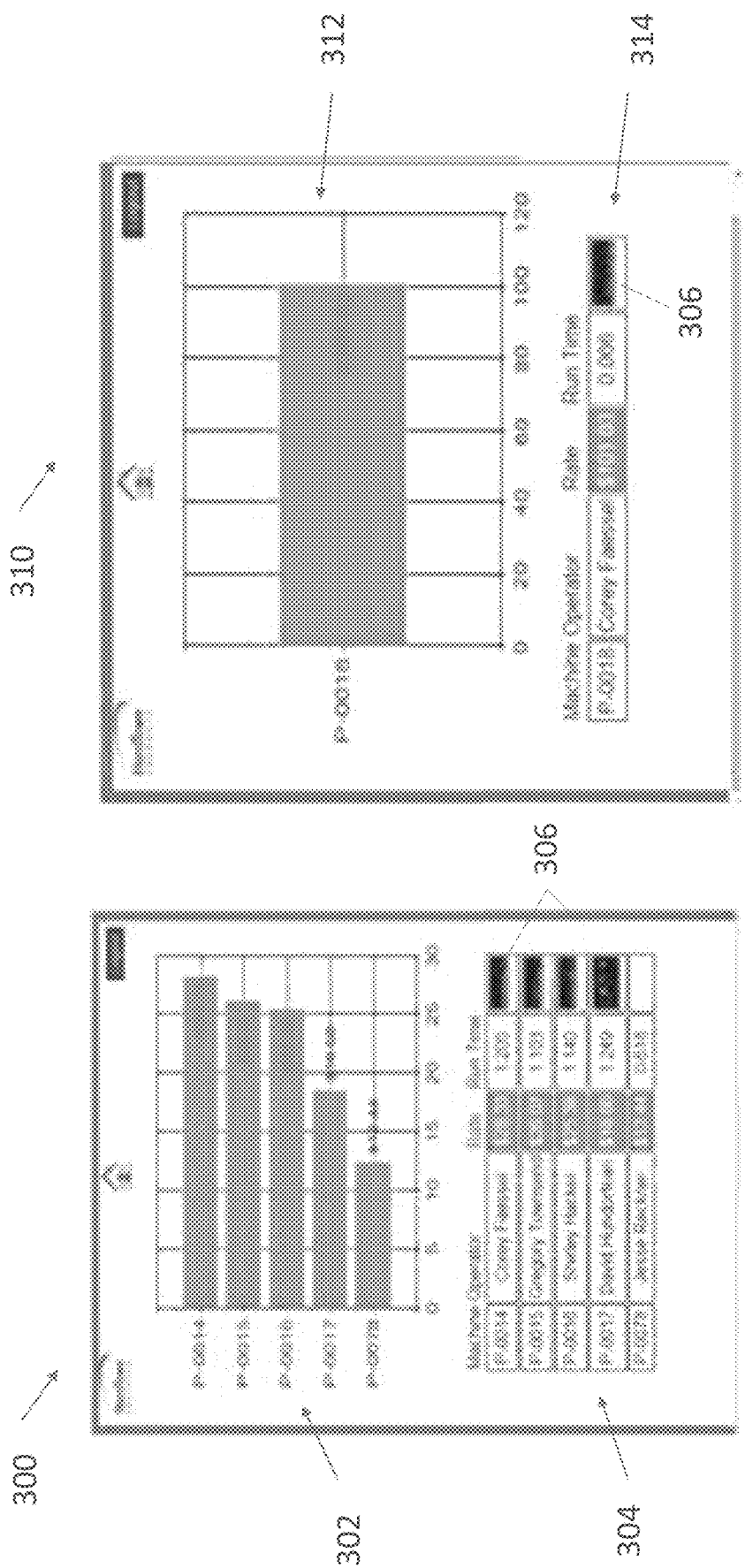
FIG. 9A is an exemplary user interface.
FIG. 9B is another exemplary user interface.

FIG. 9A is an exemplary user interface 300 for use with the challenge system 200. The illustrated user interface 300 may be utilized, for example without limitation, on the display 202. The user interface 300 may comprise a ranking of employees 304. The ranking 304 may list the machine 20 associated with the employee, the employee's name, the employee's real-time-pay rate, the amount of time the employee has been working, and a graphic. The ranking 304 may be organized to rank machines 20 and/or employees from highest to lowest in terms of their real-time-pay rate. The information in the ranking 304 may be updated periodically, or in substantially real-time. The graphic may be updated to reflect the real-time-pay rate. For example, without limitation, the graphic may comprise flames when the real-time-pay rate reaches a first pre-determined threshold, the graphic may comprise fireworks when the real-time-pay rate reaches a second pre-determined threshold, and the graphic may comprise a photo of the employee when the real-time-pay rate reaches a third predetermined threshold.

The user interface 300 may further comprise a visualization 302 illustrating the ranking 304. For example, the visualization 302 may comprise a chart, such as but not limited to, a bar chart indicating the machine 20 and/or the employee's name and the associated real-time-pay rate. The visualization 302 may be organized to rank machines 20 and/or employees from highest to lowest in terms of their real-time-pay rate. Any type of kind of visualization 302 is contemplated.

FIG. 9B is another exemplary user interface 310. In exemplary embodiments, without limitation, the user interface 310 may be displayed on an individual machine 20. The user interface 310 may, but is not required to, be similar to the user interface 300 but with information 314 pertaining to a single machine 20 or employee. For example, without limitation, the user interface 310 may comprise the machine 20 number, the employee name, the employee's real-time-pay rate, the machine's 20 run time, and a graphic 306 reflecting the real-time-pay rate. The user interface 310 may further comprise a visualization 312 illustrating the employee's real-time-pay rate. The visualization 312 may be, but is not limited to, a bar chart. Any type of kind of visualization 312 is contemplated. In exemplary embodiments, the user interface 310 may be displayed on an individual machine 20 while the user interface 300 is displayed on the display 202, though such is not required. In exemplary embodiments, both the user interfaces 300 and 310 are controlled by the challenge system 200, though such is not required.

Figure 10:
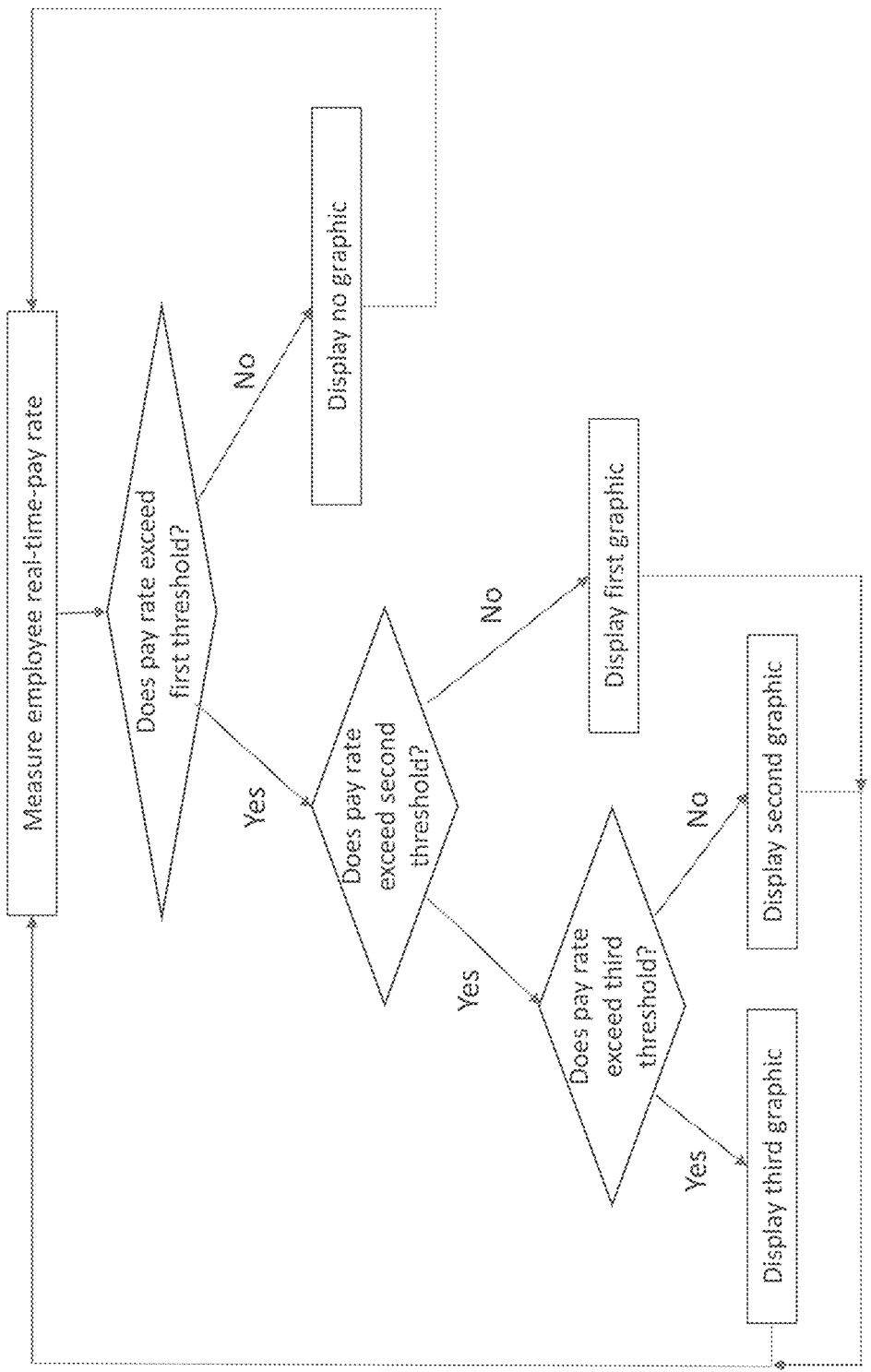
FIG. 10 is a flow diagram illustrating exemplary logic for challenges.

FIG. 10 is a flow diagram illustrating exemplary logic for challenges. Such challenges may, for example, indicate the employee's progress or metrics relative to peers or co-workers. The real-time-pay rate for the employee and/or machine 20 may be determined. If the real-time-pay rate exceeds a first threshold, a first graphic 306 may be displayed. If the real-time-pay rate exceeds a second threshold, a second graphic 306 may be displayed. If the real-time-pay rate exceeds a third threshold, a third graphic 306 may be displayed. Any number of pre-determined thresholds are contemplated and any number of graphics 306 of any kind to be displayed are contemplated. In other exemplary embodiments, other actions may be triggered at such thresholds including alerts sent to management, bonuses, achievement awards, and the like.

In exemplary embodiments, achievement in the challenge system 200 may be translated into incentives for the employee such as, but not limited to, increase in pay, bonuses, extra break time, dress down days, vacation days, or the like. It is notable that one, or a number of metrics, may be measured and compared. A positive or negative result may be provided based on each individual metric, or all metrics. Certain metrics may be weighted more of less compared to other metrics. Furthermore, different aspects of the challenge system 200 may be changed based on whether positive or negative results are found for particular metrics. For example, without limitation, an employee's virtual car in a race may be made to go faster as productivity increases, but may have a simulated tire blowout if a defective part is assembled that fails inspection. Of course, this is just one example. Such incentives may be provided by way of the banking system 111, though such is not required.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose computers of specialized computing device. The electronic devices may be personal computers, smartphone, tablets, databases, servers, or the like. The electronic connections described herein may be accomplished by wired or wireless means.

What is claimed is:

1. A system for increasing productivity of an employee performing a production activity, said system comprising:
   a machine associated with the employee and configured to assist the employee in producing units of output as part of accomplishing the production activity;

a database in electronic communication with the machine by way of an electronic interface and comprising a pay rate as well as one or more predetermined thresholds for the production activity;

a data acquiring device associated with the machine and configured to measure an actual production metric for said production activity in substantially real time from said machine, wherein said actual production metric comprises a number of the units of output produced using the machine over a period of time;

a processor adapted to retrieve the pay rate for the employee and the one or more predetermined thresholds from the database, receive the actual production metric from the data acquiring device, determine a real-time-pay rate for the employee, and determine whether the real-time-pay-rate exceeds at least one of the one or more of the predetermined thresholds, wherein said real-time-pay rate comprises an amount of pay per unit of time; and a display associated with the machine and in electronic communication with said processor, wherein said display is configured to display, in substantially real time, the real-time-pay rate and a graphic reflecting whether at least one of the one or more of the predetermined thresholds is exceeded by the employee, wherein said graphic comprises a non-numerical pictorial image, and wherein said real-time-pay rate is displayed as said amount of pay per unit of time.

2. The system of claim 1 wherein:
the display is located on the machine.

3. The system of claim 1 further comprising:
a second machine associated with a second employee and configured to assist the second employee in accomplishing the production activity, wherein the second machine is in electronic communication with the database by way of a second electronic interface; and
a second data acquiring device associated with the second machine and configured to measure a second actual production metric for said production activity in substantially real time from said second machine.

4. The system of claim 3 wherein:
the processor is adapted to receive the second actual production metric from the data acquiring device, determine a second real-time-pay rate for the second employee, and determine whether the second real-time-pay-rate exceeds at least one of the one or more of the predetermined thresholds.

5. The system of claim 4 further comprising:
a second display associated with the second machine, and configured to display, in substantially real time, the second real-time-pay rate and a second graphic reflecting whether at least one of the one or more of the predetermined thresholds has been exceeded by the second employee.

6. The system of claim 5 further comprising:
a common display associated with the machine and the second machine, wherein the common display is configured to display a relative ranking of the first and second employees by the real-time-pay rate.

7. The system of claim 6 wherein:
the common display is configured to display a visualization reflecting the real-time-pay rate of each employee associated with the production activity.

8. The system of claim 7 wherein:
the visualization comprises a bar chart reflecting the real-time-pay rate of each employee associated with the production activity.

9. The system of claim 8 wherein:
the machine and the second machine are associated with a common assembly line; and
the common display is located in a common area within direct visual range of the assembly line.

10. The system of claim 1 wherein:
the real-time-pay rate is determined by multiplying the pay rate with the actual production metric.

11. The system of claim 1 wherein:
the one or more of the predetermined thresholds comprises three predetermined thresholds, each associated with a different graphic.

12. A system for increasing employee productivity in an industrial manufacturing production activity, said system comprising:
a series of industrial manufacturing machines, each configured to accommodate an employee and assist the employee with producing tangible components as part of accomplishing an industrial manufacturing aspect of the industrial manufacturing production activity for a common assembly line, wherein each of the industrial manufacturing machines comprise a data acquiring device configured to measure actual production metrics for a respective one of the industrial manufacturing machines in substantially real time;
at least one database in electronic communication with each of the industrial manufacturing machines by way of an electronic interface and comprising a pay rate associated with each employee, predetermined production metric thresholds associated with each employee, and graphics, wherein each of the graphics is associated with one of the predetermined production metric thresholds and comprise non-numerical, pictorial images;
one or more processors in electronic communication with each of the data acquiring devices and each of the at least one database and adapted to, for each of the employees associated with each of the industrial manufacturing machines, receive the actual production metrics from each of the data acquiring devices, retrieve the pay rate and predetermined production metric thresholds associated with each of the employees, determine a real-time-pay rate for each of the employees as said actual production metrics are received, wherein each of said real-time-pay-rates are determined based on at least a most recently received one of said actual production metrics and the retrieved pay rate for a respective one of said employees, determine whether the real-time-pay-rate exceeds one or more of the retrieved predetermined thresholds, and retrieve an associated one of the graphics where the real-time-pay-rate exceeds at least one of the one or more of the retrieved predetermined thresholds, wherein said one or more processors is further configured to generate a ranking of each of the employees based on the real-time-pay-rate for each of the employees; and
a common display associated with the one or more processors, wherein the display is configured to, in substantially real time, display said ranking, a bar chart reflecting the real-time-pay rate for each employee, and the retrieved associated one of the graphics for each employee.

13. The system of claim 12 wherein:
the common display is located remote from each of the industrial manufacturing machines; and the common display is located within visual range of each of the industrial manufacturing machines on the common assembly line.

14. The system of claim 12 wherein:
the actual production metric for each employee comprises the number of units processed by the respective industrial manufacturing machine over a period of time; and
the real-time-pay rate for each employee is determined by multiplying the employee's pay rate with the actual production metric.

15. The system of claim 12 further comprising:
a number of individual displays, each associated with one of the industrial manufacturing machines and configured to display the real-time-pay rate of the employee associated with the respective industrial manufacturing machine.

16. A method for increasing employee productivity in a production activity, said method comprising the steps of:
providing a series of machines, each associated with an employee, for producing units of output as part of accomplishing the production activity;
storing, at a database in electronic communication with each of the machines, a pay rate for each employee for the production activity and one or more predetermined thresholds associated with each employee;
monitoring, by way of data acquiring devices, each associated with one of the machines, an actual production metric for each of said machines for said production activity in substantially real time, wherein each of said actual production metrics comprises a number of the units of output produced using a respective one of the machines over a period of time;
retrieving the pay rate for each employee from the database;
receiving the actual production metric for each employee from the respective data acquiring device;
determining, at the processor, a real-time-pay rate for each employee based on the actual production metric and the pay rate for the employee, wherein each of said real-time-pay rates comprise an amount of pay per unit of time; and
displaying, at a display associated with each of the machines, in substantially real-time, a ranking of each employee comprising the real-time-pay rate for each employee, a visualization reflecting the real-time-pay rate of each employee, and a graphic indicating whether the real-time-pay rate for each employee exceeds one or more of the predetermined thresholds, wherein said graphic comprises a non-numerical, pictorial image, and wherein said real-time-pay rate is displayed as said amount of pay per said unit of time.

17. The method of claim 16 wherein:
said visualization comprises a bar chart reflecting the real-time-pay rate of each employee.

18. The method of claim 17 further comprising the steps of:
the display is located remote from each of the series of machines.

19. The method of claim 18 wherein:
the pay rate and the predetermined thresholds are the same for each employee.

* * * * *